United States Patent [19]

Furuya et al.

[11] 4,446,580
[45] May 8, 1984

[54] PROSTHETIC FOOT STRUCTURE

[75] Inventors: Koutaro Furuya, Tokyo; Kazuho Hosoda, Saitama; Takahito Takeuchi, Tokyo; Yasuyuki Ishikura, Tokyo; Morihiro Kameda, Tokyo, all of Japan

[73] Assignee: Keiai Orthopedic Appliance Co., Ltd., Tokyo, Japan

[21] Appl. No.: 272,067

[22] Filed: Jun. 9, 1981

[51] Int. Cl.³ .............................................. A61F 1/08
[52] U.S. Cl. ................................................... 3/6
[58] Field of Search ................... 3/33, 35, 30, 31, 32, 3/6, 6.1, 7, 8, 2, 5

[56] References Cited

U.S. PATENT DOCUMENTS

| | | | |
|---|---|---|---|
| 1,198,399 | 9/1916 | Babcock | 3/6.1 |
| 1,294,632 | 2/1919 | Dickson | 3/7 |
| 3,196,423 | 7/1965 | Farneth | 3/32 |
| 3,206,235 | 9/1965 | Albinson et al. | 3/21 UX |
| 3,414,908 | 12/1968 | Waggott et al. | 3/71 |
| 4,038,705 | 8/1977 | Owens et al. | 3/21 X |
| 4,145,765 | 3/1979 | Malone | 3/7 |

FOREIGN PATENT DOCUMENTS

| | | | |
|---|---|---|---|
| 576867 | 5/1958 | Italy | 3/7 |
| 1550658 | 8/1979 | United Kingdom | 3/21 |

Primary Examiner—Richard J. Apley
Assistant Examiner—David J. Isabella
Attorney, Agent, or Firm—Fleit, Jacobson, Cohn & Price

[57] ABSTRACT

A foot section of the artificial limb comprising a base, a housing pivotally connected to the base to form an ankle joint, a shaft pivotally connected to the other portion of the base and extending into the housing, and a bumper device for adjusting a heel-height of the foot regardless of change of the heel-height. A pivotal axis of the housing relative to the base is positioned on a line which lies intermediate an axial line of the shaft and a toe break of the foot.

5 Claims, 8 Drawing Figures

PROSTHETIC FOOT STRUCTURE

BACKGROUND OF THE INVENTION

The present invention relates to the foot section of an artificial leg or limb and more particularly to a prosthetic foot having an ankle meeting varied requirements of different patients.

Heretofore the artificial limbs have been developed but still have disadvantages. For example, in respect of the foot section, i.e., the prosthetic foot, an alignment angle of the prosthetic foot has been determined at hospitals and/or medical institutions and adjusted according to the condition of patients with putting shoes on. The patients, however, usually occupy much time for walking with bare feet and walking up and down on the sloped floor or the like in their daily life, and the patients have to feel inconvenience with their previously fixed elements of the prosthetic foot. For instance, the patients must cope with the inconvenience through standing and walking on tiptoe, supplementing an element or elements which have the same heel height as the shoes they put on.

SUMMARY OF THE INVENTION

An object of the present invention is to provide an improved prosthetic foot which permits an automatic adjustment of the heel height without employing additional elements.

Another object of the present invention is to provide a prosthetic foot which permits a natural, smooth walking with shoes on and with bare feet.

A further object of the present invention is to provide a prosthetic foot which provides the patients a pleasant feeling of walking in the cases of uphill walking and downhill walking.

Briefly, the foot section of the artificial limb according to the present invention has a base having a forward projection, a housing pivotally connected to the forward projection of the base to form an ankle axis of the foot section to which patient's substantial weight is applied, a shaft pivotally extending from the base into the housing, and a bumper device disposed around the shaft. The housing is connected to other upper section such as a shin section of the artificial limb and inclinable about the ankle axis relative to the base. The ankle axis lies on a middle point between an axis of the shaft and a toe break wherein the toe break represents a fore end of a plantar arc of the foot.

The bumper device may be formed with a spiral spring around an upper portion of the shaft and a cylindrical member of a resilient synthetic resin, the cylindrical member being disposed around the lower portion of the shaft. The bumper device may be formed with a single cylindrical member of a resilient synthetic resin. The shaft may be formed with two sections so as to maintain its central position within the housing.

DETAILED DESCRIPTION OF THE INVENTION

Figure 1:
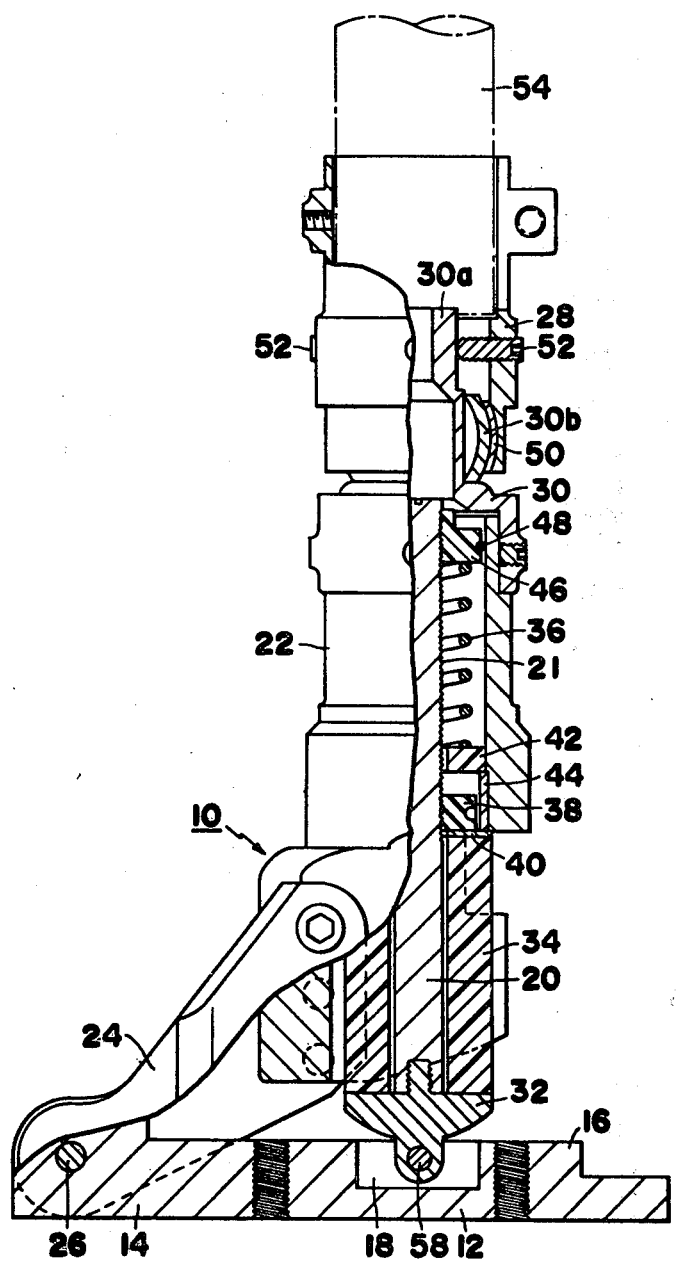
FIG. 1 is a fragmentary sectional view of the artificial leg section, i.e., prosthetic foot, embodying the present invention.

Like reference numerals represent like parts throughout various figures of the drawings.

Figure 2:
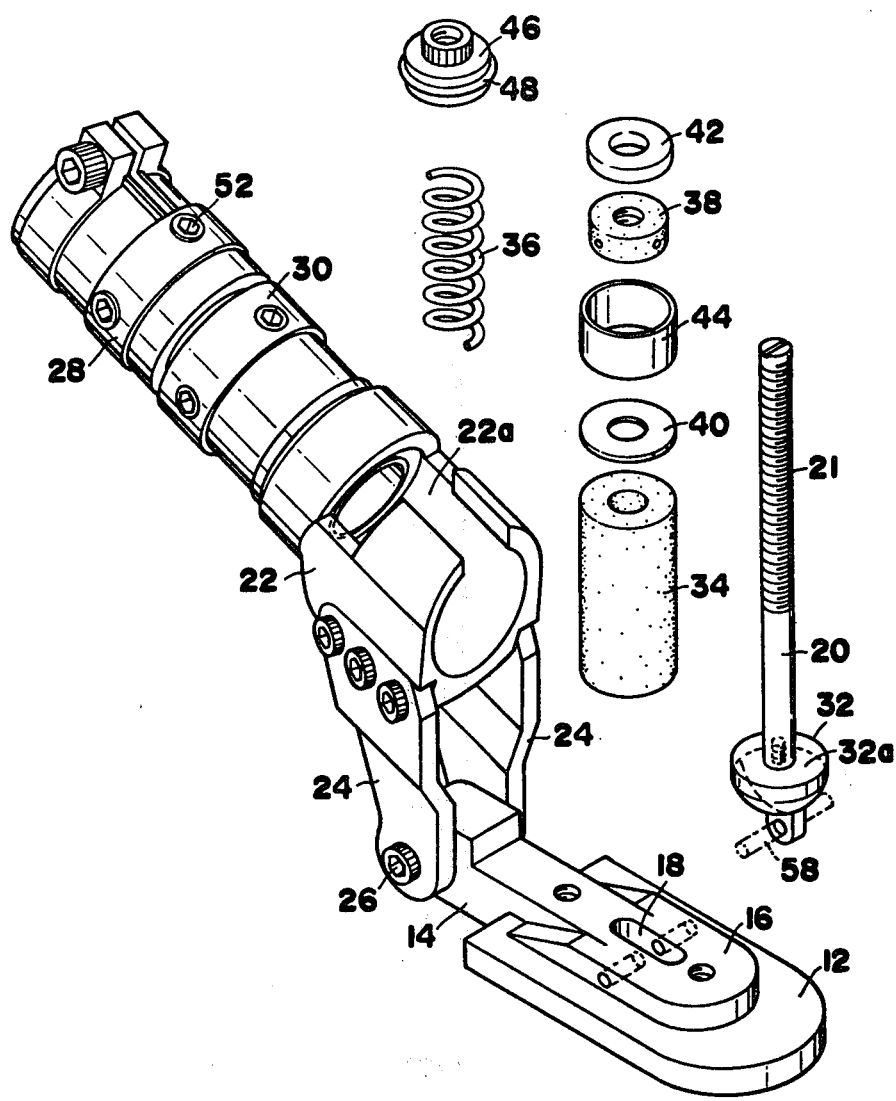
FIG. 2 is an exploded, perspective view of the components of the prosthetic foot shown in FIG. 1.
Figure 3:
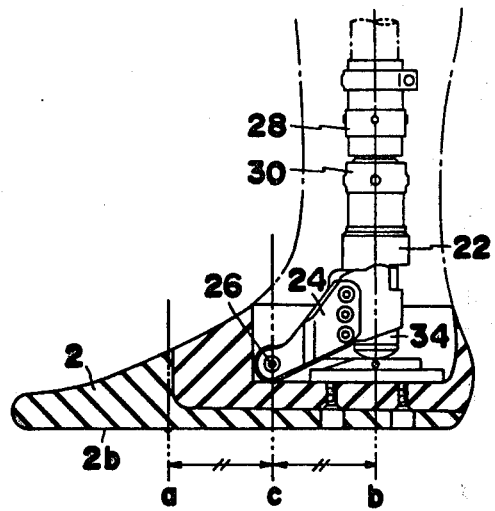
FIG. 3 is a side view of the prosthetic foot assembled in position to form a completed foot, showing a standing posture of the foot.

Referring to FIGS. 1 to 3, reference numeral 10 represents in general an inventive prosthetic foot structure which has a base 12 having a projection 14 extending from a fore end of the base 12 and a heel portion 16 having an elongated recess 18 for pivotally holding a mechanically axial shaft 20 which will be described. The base 12 is connected to a cylindrical housing 22 through a pair of arms 24 which extend to, and pivotally connected to, the projection 14 by means of a pin 26, the pin being a true axis of ankle joint of the inventive prosthetic foot structure. The housing 22 is connected at its upper end to a socket 28 through a connector 30. As illustrated in the drawing, the axis 26 of the ankle is positioned at a fore portion relative to the mechanical axis constituted by the shaft 20, while the conventional prosthetic foot has a true ankle axis on the mechanical axis of shaft. The axis 26 is positioned intermediate the mechanical axis, which is shown by reference "b" in FIG. 3, and a so-called toe break point (a) which is a fore end point of a plantar arc.

Within the housing are provided an elongated shaft 20 which has a threaded groove 21 at its upper portion and a supporter 32 at its lower end, a tubular heel bumper 34 and a dorsiflexion bumper 36 of a coil spring. As shown, the heel bumper 34 is mounted on the supporter 32, which is threadedly engaged with the shaft 20, and around a lower portion of the shaft 20 while the dorsiflexion bumper 36 is mounted within the upper portion of the housing 22. More specifically, the heel bumper 34 is disposed on a flat upper portion 32a of the supporter 32 such that its upper end is adjustably limited by a pressure adjustment ring 38 through a washer 40, the pressure adjustment ring 38 is threadedly engaged with the shaft 20 and can be manipulated by a suitable tool (not shown) through a window 22a of the housing 22. Above the pressure adjustment ring 38 is disposed a seat 42 placed on a cylindrical member 44 having a height greater than that of the pressure adjustment ring 38. The aforesaid dorsiflexion bumper 36 is positioned between the seat 42 and a stopper 46 threadedly engaged with the upper portion of the shaft 20. The stopper 46 has an annular member 48 on its outer surface for facilitating a smooth movement of the stopper 46 within the cylindrical housing 22.

The connector 30 which is connected to the upper end of the housing 22 has a tubular extension 30a of reduced diameter which is in a coaxial relation with the shaft 20, and a supporting ring 30b around a middle portion of the connector 30. The supporting ring 30b is fixed to the middle portion of the connector 30 and has an arc shaped cross section as illustrated in FIG. 1. The socket 28 which has a bearing 50 at the inner lower end thereof is movably mounted on the supporting ring 30b of the connector 30, and movably and adjustably fixed to the connector 30 by manipulating bolts 52 against the tubular extention 30a. By adjusting the bolts 52, axis of the socket 28 which is connected to a pipe 54 for the shin section of the artificial limb structure can be adjusted. The thus formed ankle joint structure is assembled such that the base 12 is fixed to a bore 56a of a "foot" 2, which has a similar contour as an unartificial foot, by means of bolts so that the supporter 32 of the shaft 20 is pivotally secured by a pin 58.

Referring now to FIGS. 3 through 6, showing that the thus formed prosthetic foot is applied in use for walking with bare foot so that substantially all bottom surface 2b contacts the floor, which is designated at 3, the real axis of the foot, namely an ankle axis 26, is positioned on the line (c) which lies intermediate the toe break (a) and the mechanical axis (b) of the prosthetic foot. Accordingly, the weight or load added to the housing 22 is not applied to the heel bumper 34, and the heel bumper 34 remains its predetermined position, as shown in FIG. 3.

Figure 4:
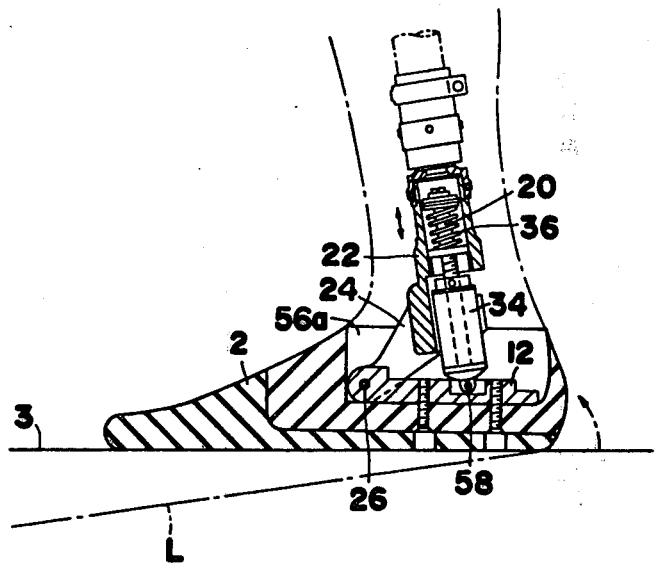
FIGS. 4 and 5 are partly sectioned views of the prosthetic foot, showing a push-off phase and a phase in which the foot contacts a floor after a swing phase.

In the push-off phase of the foot, namely at the beginning of walking, which is shown in FIG. 4, the arms 24 as well as the housing 22 are inclined forwardly about the pivotal axis 26 due to movement of patient's weight. In this instance, the shaft 20 disposed coaxially within the cylindrical portion of the housing 22 is inclined forwardly about the axis 58. Since the effective length of the shaft 20 is predetermined and the housing 22 is moved upward relative to the shaft 20 due to the inolination, the dorsiflexion bumper 36 of a spiral spring is compressed by the effect of the inclination of the housing 22. In the push-off phase of the walking, the heel bumper 34 of resilient material such as suitable synthetic resins does not receive a compression force since the angle of the arms 24 relative to the base 12 becomes larger due to inclination of the housing 22.

In a so-called swing phase which comes immediately after the aforementioned push-off phase to leave the foot from the floor to thereby maintain it in air for a successive step of walking, the angle of the arms at the pivotal axis 26 returns to the original position by the effect of the dorsiflexion bumper 36 which has been compressed, so that the shaft 20 and the housing 22 are erected upright at right angles relative to the base 12, or returned to their original posture.

Figure 5:
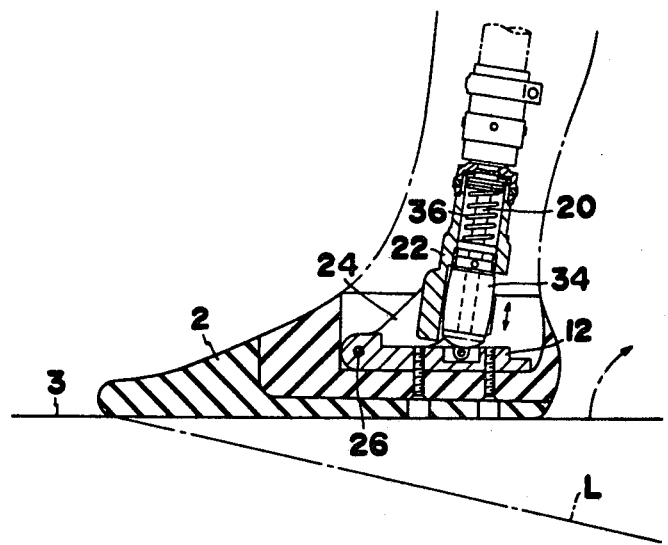

After the swing phase of walking, the foot is to be contacted with the floor again for a normal standing phase wherein the heel is contacted with the floor and slightly depressed. Namely, the base 12 is inclined relative to the arms 24 to cause the heel bumper 34 to be compressed, and this effects a sort of shock absorbing function at the time of landing of the foot after the swing phase of walking. Besides, the heel bumper 34 has a function to return the elements such as housing 22 and shaft 20 to their standing posture as shown in FIG. 3. In this instance, the dorsiflexion dumper 36, on the other hand, does not receive any load. This is illustrated in FIG. 5.

The above described pivotal movement of the ankle joint at the pivotal axis 26 is applied to the walking on a flat floor, but similar principle of movement can be obtained in case of walking up or down on the slope. This is shown by phantom lines "L" in FIGS. 4 and 5 wherein the phantom line L intends to represent a level surface while the solid line in this case represents a slope, and therefore FIG. 4 and FIG. 5 show walking up posture and walking down posture, respectively. In either cases of the up-hill walking and down-hill walking, the substantially all surface of the bottom of the foot contacts the slope in a desired posture.

Figure 6:
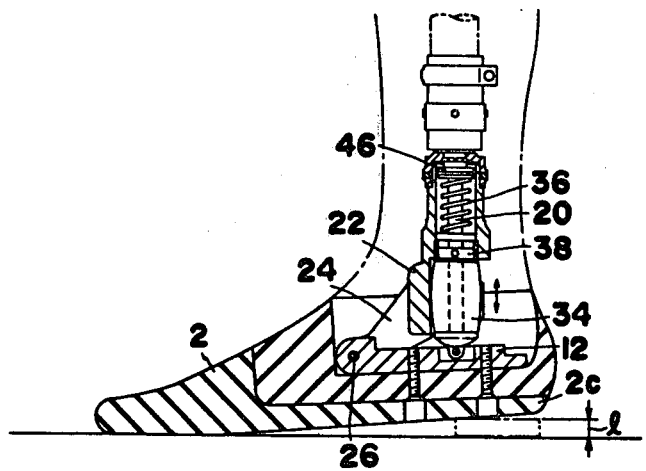
FIG. 6 is a partly sectioned view of the prosthetic foot, showing the heel being lifted up as high as the height of a shoeheel.

Referring to FIG. 6 showing a principle of the foot with a shoe on, the heel position 2c is shifted upward as high as the thickness or height of heel of, for example, 1–3 cm. In case of the foot with a shoe on, the base 12 is actually lifted upward as shown, but the heel bumper 34 is compressed, as is in the case of the down-hill walking of FIG. 5, as much as the length which corresponds to the increased thickness or height (l) of the sole of the shoe-heel. The pivotal axis 26 of the ankle joint lies on the fore position (on line "c" in FIG. 3) relative to the mechanical axis ("b" in FIG. 3), and hence the heel bumper 34 is compressed as much as the length (l) which is equivalent to the thickness of the heel. Thus, the shaft 20 stands vertical relative to the floor or ground, and the foot can be in normal walking posture. Accordingly, the patient can walk with putting shoes on in quite a normal posture without causing unpleasant tip-walking or toe-walking. Of course, the alignment, namely axial position of the shaft 20 relative to the housing 22, is fixed unchanged throughout its length. Thus, a walking with putting shoes on can be achieved without any obstacle as similar as the condition of the bare-foot walking. The resilient forces of the heel bumper 34 and of the dorsiflexion bumper 36 are adjusted by the ring 38 and the stopper 46, respectively.

According to the prosthetic foot of the present invention, the ankle axis 26 is designed to be positioned intermediate the toe break (a) and the mechanical axis (b) of the shaft 20, with the compressible heel bumper 34 and the dorsiflexion bumper 36 being mounted around the shaft 20. Accordingly, the increase of height of the heel portion as much as the height of the shoe can be absorbed by the combination of the bumpers 34 and 36. Thus, a normal walking as is in the case of bare-foot walking can be achieved. Namely, the height-change of the heel can be absorbed or supplemented by the effect of the two bumpers 34 and 36, which are effected alternately, and smooth pivotal movement of the ankle can be obtained. In case of walking up and down on the slopes, the bumpers 34 and 36 have a function as a stopper for preventing a further or excessive inclination and therefore a smooth walking can be achieved.

Figure 7:
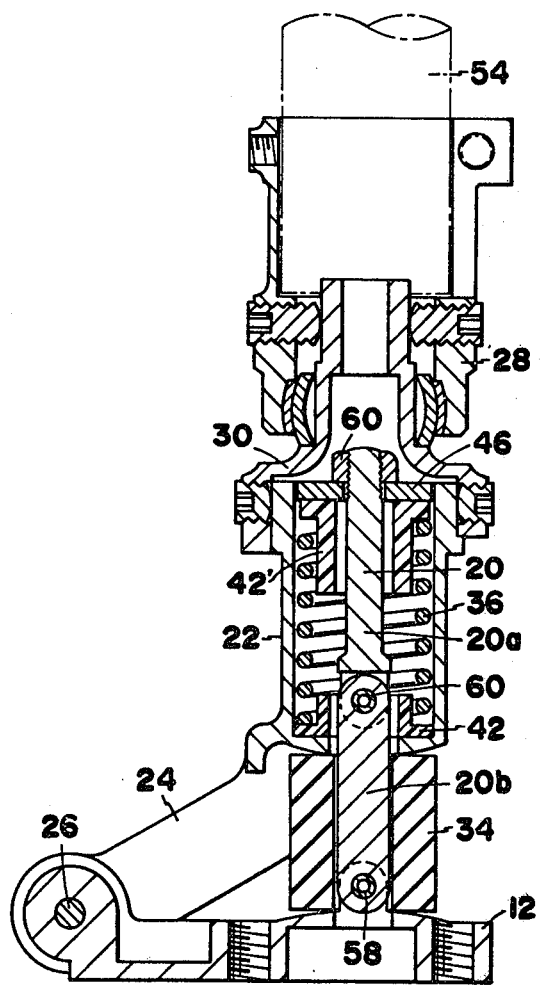
FIG. 7 is a sectional view of a prosthetic foot according to another embodiment of the invention.

FIG. 7 shows a modified foot structure in which the shaft 20 is formed with two parts 20a, 20b pivotally joined together at 60 and the heel bumper 34 is confined between a lower end of the cylindrical housing 22 and the base 12. The lower end of the housing 22 is bent inward to nest thereon the ring shaped seat 42 for the dorsiflexion bumper 36 of a spiral spring. The force of the dorsiflexion bumper 36 is adjusted by manipulating a nut 60 to move the stopper 46 and other seat 42'. The pivotal axis 61 of the shaft 20 permit the shaft to be positioned at the center of the housing 22 when the foot is in use. Other elements such as arms 24, socket 28 and connector 30 and structure as well as their function and operation are similar to these of the previous embodiment described with reference to FIGS. 1 through 6, and a detailed description will not be made.

Figure 8:
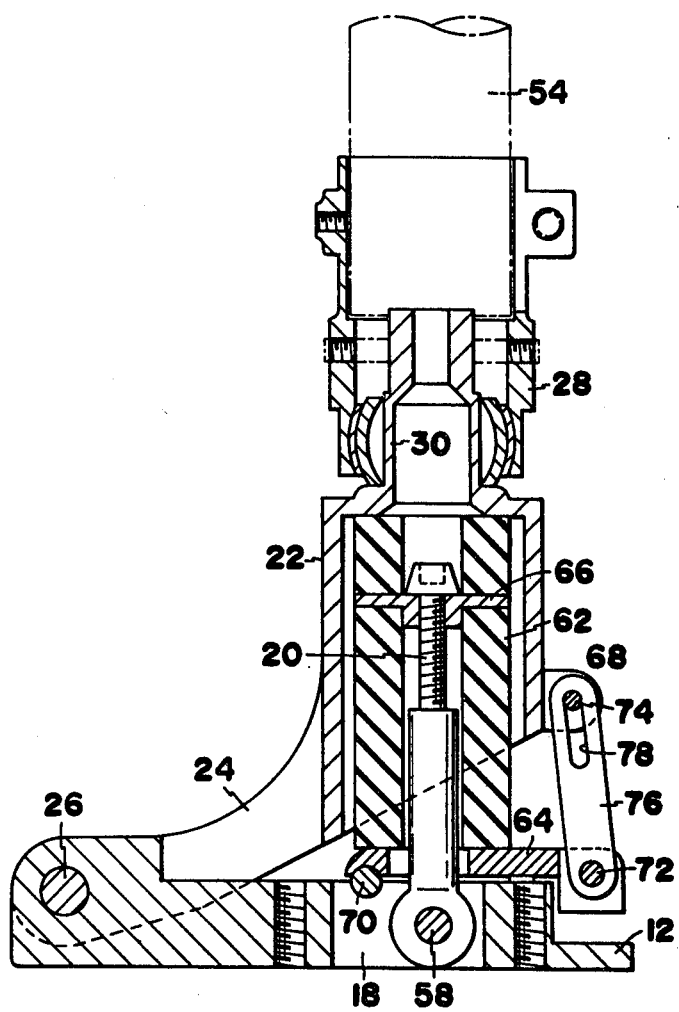
FIG. 8 is a sectional view of a further modified prosthetic foot according to the invention.

FIG. 8 shows a further modification wherein the housing 22 and connector 30 are formed in integral, and the spiral spring for dorsiflexion bumper 36 is removed. However, in this embodiment a cylindrical rubber bumper 62 has functions of the dorsiflexion bumper 36 of the previous embodiments as well as of the heel bumper 34. The cylindrical bumper 62 is placed on a lever 64 and has at its upper portion a washer 66 for securing the shaft 20. The shaft 20 can be made shorter than that of the previous embodiment since the bumper 62 has dual function. The shaft 20 is pivotally connected to the base 12 within the elongated recess 18 of the base 12 by means of the pin 58. The cylindrical housing 22 containing therein the bumper 62 has a projection 68 at the position opposite to the arms 24. The lever 64 is pivotable about an axis 70 which is fixed to the base 12, and extends rearwardly. The lever 62 has at its rear end a pin 72 while the projection 68 has a pin 74. A link 76 is connected at its lower end to the lever 64 by means of a pin 72, and the upper portion of the link 76 has an elongated slot 78 for movably securing the pin 72.

In the push-off phase as is illustrated in FIG. 4, the dual functioning bumper 62 as well as the housing 22 is inclined forwardly to thereby raise the lever 64 by means of the link 76. Thus, the lever 64 is lifted upward at the axis 70. In this case the pin 74 is positioned at the upper end of the elongated slot 78. The other structure and functions are similar to those of the previous embodiments and will be understood from the foregoing description and detailed description will not be made.

Though the present invention has been described with reference to preferred embodiments, many modifications and alterations can be made within the spirit of the invention.

What is claimed is:

1. A foot section of an artificial limb comprising:
   (a) a horizontal base member having a longitudinal axis defining thereon a forward projection, a heel portion, and a first pivot axis, said forward projection having a second pivot axis at a forward end wherein said first and said second pivot axes are horizontally perpendicular to said longitudinal axis;
   (b) a housing having a cylindrical portion and pivotally connected to an arm extending therefrom to said base member at said second pivot axis forming an ankle axis of the foot section;
   (c) a shaft pivotally connected to said base member at said first pivot axis and extending coaxially through a resilient member mounted to said housing thereby permitting said housing to incline about said second pivot axis toward said forward projection;
   (d) said resilient member includes a first bumper which is compressed upon inclining of said housing toward said forward projection, and a second bumper for effecting absorption of compressive forces added to the heel portion of the foot section so that a smooth walking phase can be achieved; and
   (e) wherein said second pivot lies on a line which is intermediate the first pivotal axis and a line corresponding to the foremost part of the plantar arc of a human foot.

2. The foot section according to claim 1, in which said first bumper is a dorsiflexion bumper including a spiral spring device and said second bumper is a heel bumper including a cylindrical member made of resilient plastic materials, said first bumper being mounted around an upper portion of said shaft and above said second bumper.

3. The foot section according to claim 2, in which said foot section has a socket for inteconnecting said housing and a shin section of the artificial limb, said housing being adjustably connected to said socket.

4. The foot section according to claim 3, in which a connector is disposed between said socket and said housing, wherein said socket has a bearing having an arc shaped cross section and said connector has an annular member having an arc shaped cross section, said bearing being adjustably mounted to said annular member such that said socket can be adjusted relative to an axis of said shaft.

5. The foot section according to claim 1, in which said shaft has an upper part and a lower part, said upper part being pivotally connected to said lower part.

* * * * *